(12) United States Patent
Che

(10) Patent No.: US 8,722,897 B2
(45) Date of Patent: May 13, 2014

(54) METAL COMPLEXES OF THIOUREA AND DERIVATIVES AS METAL DELIVERING ANTI-CANCER AND ANTI-INFLAMMATORY AGENTS

(76) Inventor: Chi Ming Che, Hong Kong (CN)

( * ) Notice: Subject to any disclaimer, the term of this patent is extended or adjusted under 35 U.S.C. 154(b) by 170 days.

(21) Appl. No.: 13/091,625

(22) Filed: Apr. 21, 2011

(65) Prior Publication Data
US 2011/0269730 A1    Nov. 3, 2011

Related U.S. Application Data

(60) Provisional application No. 61/328,829, filed on Apr. 28, 2010.

(51) Int. Cl.
*C07F 1/12* (2006.01)
*C07F 1/08* (2006.01)
*C07F 1/10* (2006.01)
*C07F 1/00* (2006.01)

(52) U.S. Cl.
CPC . *C07F 1/12* (2013.01); *C07F 1/005* (2013.01); *C07F 1/08* (2013.01); *C07F 1/10* (2013.01)
USPC .................................................. 548/105

(58) Field of Classification Search
CPC .............. C07F 1/12; C07F 1/005; C07F 1/08; C07F 1/10
USPC ....................................................... 548/105
See application file for complete search history.

(56) References Cited

FOREIGN PATENT DOCUMENTS

CN         101260121       9/2008

OTHER PUBLICATIONS

Yan et al. "Gold(I) complex of N,N'-disubstituted cyclic thiourea with in vitro and in vivo anticancer properties—potent tight-binding inhibition of thioredoxin reductase" Chem Commun, 2010, pp. 7691-7693.*
Dash et al. CAS Accession No. 1973:511293 (1973).*
Graybeal et al. "Nuclear quadrupole coupling of copper nuclei in coordination compounds of copper(I) with thiourea and substituted thioureas" Inorganic Chemistry, 1972, vol. 11, pp. 3104-3106.*
Hartung et al. CAS Accession No. 1980:504774.*
J.F. Morrison and C.T. Walsh, Advances in Enzymology and Related Areas of Molecular Biology, 1988, 61, 201-301.
R. Uson, A. Laguna, M. Laguna, *Inorg. Syn.* 1989, 26, 85-91.
G. J. Kubas, *Inorg. Syn.* 1990, 28, 68-70.
Berners Price, S.J. et al., Coordination Chemistry of Metallodrugs: Insights Into Biological Speciation from NMR Spectroscopy, Coordination Chemistry Reviews, 151 (1996), 1-40.
Zhang, Christiana Xin, et. al., New Metal Complexes as Potential Therapeutics; Current Opinion in Chemical Biology, 2003, 7, 481-489.

Sun, Raymond Wait-Yin et al., Some Uses of Transition Metal Complexes as Anti-Cancer and anti-HIV Agents, Dalton Trans., 2007, 4884-4892.
Shaw, C. Frank III, Gold-Based Therapeutic Agents, Chem Rev. 1999, 99, 2589-2600.

(Continued)

*Primary Examiner* — Joseph Kosack
(74) *Attorney, Agent, or Firm* — Robert D. Katz, Esq.; Eaton & Van Winkle LLP

(57) ABSTRACT

The present invention relates to metal thiourea complexes comprising N-substituted thiourea ligands and sulfur-coordinated metal ions, and methods for using the metal thiourea complexes for delivering otherwise unstable or impermeable metal ions to mammalian cells, for inhibiting cancer cell growth and inflammation, and for inhibiting the activities of associated drug targets under in vitro and in vivo conditions. The metal complexes of N-substituted thiourea are defined by the following formula (Ia or Ib) wherein $R_1$ can be H, alkyl, alkenyl, alkynyl, aryl or heterocyclic groups; $R_2$ can be H, alkyl, alkenyl, alkynyl or aryl groups; n=1 to 4; $X^-$ is a pharmaceutically acceptable anion (chloride, bromide, iodide, hexafluorophosphate, or triflate) and M is a coinage metal (Au, Ag, or Cu).

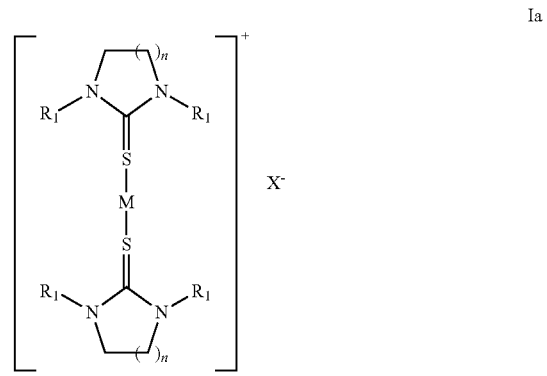
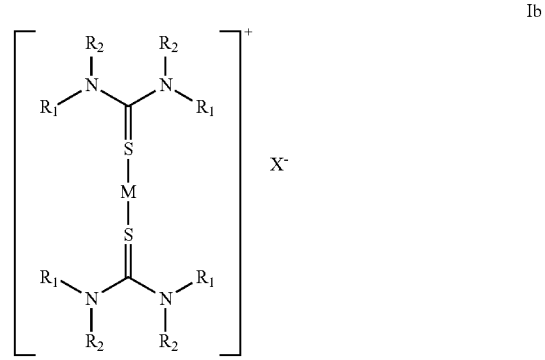

4 Claims, 10 Drawing Sheets

(56) References Cited

OTHER PUBLICATIONS

Barnard, Peter J. et al., Targeting the Mitochondrial Cell Death Pathway With Gold Compounds, Corodination Chemistry Reviews 251 (2007) 1889-1902.

Berners-Price, Susan J., Cytotoxicity and Antitumor Activity of Some Tetrahedral Bis(disphosphino) Gold (I) Chelates,Jounral of Medicinal Chemistry, 1990, 33, 1386-1392.

McKeage, Mark J., Antitumor Activity of Gold(I), Silver(I) and Copper(I) Complexes Containing Chiral Tertiary Phosphines, Metal Based Drugs, 1998, 5, 217-223.

Tiekink, Edward R.T., Phosphinegold(I) Thiolates—Pharmacological Use and Potential, Bioinorgic Chemistry and Applications, 2003, 53-67.

Barnard, Peter J. et al., Mitochondrial Permeability Transition Induced by Dinuclear Godd(I)-Carbene Complexes: Potential New Antimitochondrial Antitumour Agents; Journal of Inorganic Biochemistry, 98,(2004) 1642-1647.

Hindi, Khadijah M., Synthesis, Stability, and Antimicrobial Studies of Electronically Tuned Silver Acetate N-Heterocyclic Carbenes, Journal of Medicinal Chemistry, 2008, 51, 1577-83.

Teyssot, Marie-Laure et al., Chemistry a European Journal, 15, € 314-18 (2009) Toxicity of Copper(I)-NHC ComplexesTiekink, Edward R.T., Phosphinegold(I) Thiolates—Pharmacological Use and Potential, Bioinorgic Chemistry and Applications, 2003, 53-67.

S. Ray, R. Mohan, J. K. Singh, M. K. Samantaray, M. M. Shaikh, D. Panda and P. Ghosh, Anticancer and Antimicrobial Metallopharmaceutical Agents Based on Palladium, Gold, and Silver N-Heterocyclic Carbene Complexes, Journal of the American Chemical Society, 2007, 129, 15042-15053.

L. C. Porter, J. P. Fackler, J. Costamagna and R. Schmidt, Structure of Bis(thiourea) gold (I) Bromide, [Au{SC(NH2)2}2]Br, Acta Crystallographica Section C-Crystal Structure Communications, 1992, 48, 1751-1754.

O. E. Piro, E. E. Castellano, R. C. V. Piatti, A. E. Bolzan and A. J. Arvia, Two thiourea-containing gold (I) complexes, Acta Crystallographica Section C-Crystal Structure Communications, 2002, 58, M252-M255.

E. R. Tiekink, Anti-Cancer potential of gold complexes Inflammopharmacology, 2008, 16, 138-142.

S. S. Gunatilleke and A. M. Barrios, Inhibition of Lysosomal Cysteine Proteases by a Series of Au (I) Complexes: A detailed Mechanistic Investigation Journal of Medicinal Chemistry, 2006, 49, 3933-3937.

D. Krishnamurthy, M. R. Karver, E. Fiorillo, V. Orru, S. M. Stanford, N. Bottini and A. M. Barrios, Gold (I)-Medicated Inhibition of Protein Tyrosine Phosphatases: A Detailed in Vitro and Cellular Study, Journal of Medicinal Chemistry, 2008, 51, 4790-4795.

S. Gromer, L. D. Arscott, C. H. Williams, Jr., R. H. Schirmer and K. Becker, Human Placenta Thioredoxin Reductase, The Journal of Biological Chemistry, 1998, 273, 20096-20101.

M. P. Rigobello, G. Scutari, A. Folda and A. Bindoli, Mitochrondrial thioredoxin reductase inhibition by gold (I) compounds and concurrent stimulation of permeability transition and release cytochrome c Biochemical Pharmacology, 2004, 67, 689-696.

E. S. Arner and A. Holmgren, The thioredoxin system in cancer, Seminars in Cancer Biology, 2006, 16, 420-426.

S. Urig and K. Becker, On the potential of thioredoxin reductase inhibitors for cancer therapy, Seminars in cancer biology, 2006, 16, 452-465.

M. J. Sculley, J. F. Morrison and W. W. Cleland, Slow-binding Inhibition: the general case, Biochimica et Biophysica Acta, 1996, 1298, 78-86.

J. R. Kim, H. W. Yoon, K. S. Kwon, S. R. Lee and S. G. Rhee, Identification of Proteins Containing Cysteine Residues That are Sensitive to Oxidation by Hydrogen Peroxide at Neutral pH of Anal. Biochem, 2000, 283, 214-221.

J. Fang and A. Holmgren, Inhibition of Thioredoxin and Thioredoxin Reductase by 4-Hydroxy-2-nonenal in Vitro and in Vino, Journal of the American Chemical Society, 2006, 128, 1879-1885.

J. L. Hickey, R. A. Ruhayel, P. J. Barnard, M. V. Baker, S. J. Berners-Price and A. Filipovska, Mitochondria-Targeted Chemotherapeutics: The Rational Design of Gold (I) N-Heterocyclic Carbene Complexes That Are Selectively Toxic to Cancer Cells and Target Protein Selenols in Perference to Thiols, Journal of the American Chemical Society, 2008.

R. Uson, A. Laguna, M. Laguna, (Tetrahydrothiophene) Gold (I) or Gold (III) Complexes, Inorg. Syn. 1989, 26, 85-91.

G. J. Kubas, Tetrakis (Acetonitrile) Copper(1+) Hexafluorophosphate (1−) Inorg. Syn. 1990, 28, 68-70.

A. J. Arduengo, R. Krafczyk, R. Schmutzler, H. A. Craig, J. R. Goerlich, W. J. Marshall, M. Unverzagt, Imidazolylidenes, Imidazolinylidenes and Imidazolidines, Tetrahedron 1999, 55, 14523-14534.

D. Yang, Y. C. Chen, N. Y. Zhu, Sterically Bulky Thioureas as Air- and Moisture-Stable Ligands for Pd-Catalyzed Heck Reactions of Arly Halides Organ. Lett. 2004, 6, 1577-1580.

Chang, C. F.; Ho, C. W.; Wu, C. Y.; Chao, T. A.; Wong, C. H.; Lin, C. H., Discover of Picomolar Slow Tight-Binding Inhibitors of a-Fucosidase, Chem X Biol 2004, 11, 1301-6.

Vathipadiekal, V.; Rao, M. Inhibition of 1, 4-β-D-Xylanhydrolase by the Specific Aspartic Protease Inhibitor Pepstatin, J. Biol. Chem. 2004, 279, 47024-33.

Xu, C.; Hall, R.; Cummings, J.; Raushel, F. M. Tight binding Inhibitors of N-Acyl Amino Sugar and N-Acyl Acid Deacetylases, J. Am. Chem. Soc. 2006, 128, 4244-5.

Koh, C. Y.; Kazimirova, M.; Trimnell, A.; Takac, P.; Labuda, M.; Nuttall, P. A.; Kini, R. M., Variegin, A Novel Fast and Tight Binding Thrombin Inhibitor from the Tropical Bont Tick, J. Biol. Chem. 2007, 282, 29101-13.

R. M.R. Snyder, C. K. Mirabelli and S. T. Crooke, The Celluar Pharmacology of Aurnofin Seminars in arthritis and rheumatism, 1987, 17, 71-80.

Yin/ Kun et al., Gold(I) complex of W.Af-disubstituted cyclic thiourea with in vitro and in vivo anticancer properties—potent tight-binding inhibition of thioredoxin reductase. Chemical Communications, Nov. 7, 2010, vol. 46, No. 41, pp. 7691-7693, ISSN: 1359-7345.

Dash, R. N. eta]., Complexes of Silver(I) Perchlorate & Nitrate with Substituted Thioureas.Indian J. Chem. Jun. 1973, vol. 11, pp. 603-604 (abstract only).

Chaurasia, M. R. et al., Metal Complexes of N-Phenyl-N'-p-Bromophenyl Thiourea. Indian J. Chem. Soc. Sep. 1979, vol. LVI, pp. 922-923 (abstract only).

Sola, J. et al., Hydrogen-Bonded Network and Layered Supramolecular Structures Assembled from ClO$_4$-Counterfoils with Unprecedented Monomeric (AgLJ* $^{an}$d Chain Polymeric [AgL$_2$]$_B$$^{n*}$ Complex Cations (L=Thioamide or Thiourea-Like Ligands), Eur. J. Inorg. Chem. Oct. 2004, No. 24, pp. 4871-4881.

Bowmaker, G A. et al., Crystal Structures and Vibrational Spectroscopy of Copper(I)Thiourea Complexes, Inorganic Chemistry, 2008, vol. 48, pp. 350-368.

Isab, A. A. et al., Synthesis of silver(I) complexes of thiones and their characterization by $^{13}$C, $^{13}$N and $^{107}$Ag NMR spectroscopy, Polyhedron, Jun. 2002, vol. 21, No. 12-13, pp. 1267-1271.

Creighton, J. R. et al., Copper(I) Halide Complexes of Imidazole Thiones: Crystal Structure of Dimeric Monochloro bis(1-methylimidazoline-2-thione) Copper(I), Inorganica Chimica Acta, 1985, vol. 103, No. 2, pp. 195-205.

Akrivos, P. D. Recent studies in the coordination chemistry of heterocyclic thiones and thionates. Coordination Chemistry Reviews. Mar. 2001, vol. 213, No. 1, pp. 181-210.

Gandin, V. et al., Cancer cell death induced by phosphine gold(I) compounds targeting thioredoxin reductase, Biochemical Pharmacology, Jan. 15, 2010, vol. 79, No. 2, pp. 90-101.

Jun. 21, 2011 International Search Report in Counterpart International Application No. PCT/CN2011/000681.

* cited by examiner

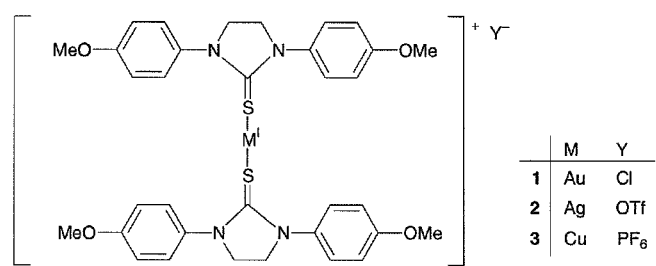
Fig. 1 Metal complexes of 1,3-bis(4-methoxyphenyl)imidazolidine-2-thione, M(TU)$_2$Y

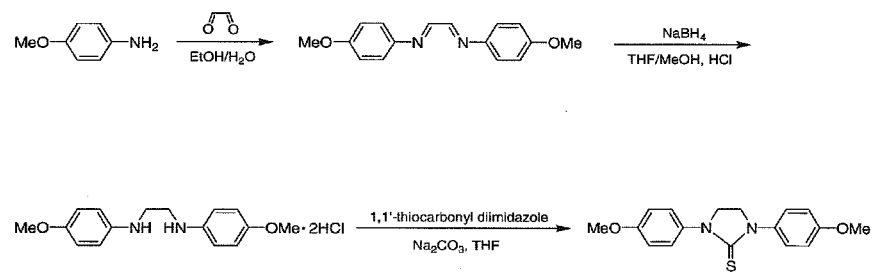
Fig. 2 Synthesis route for the thiourea ligand.

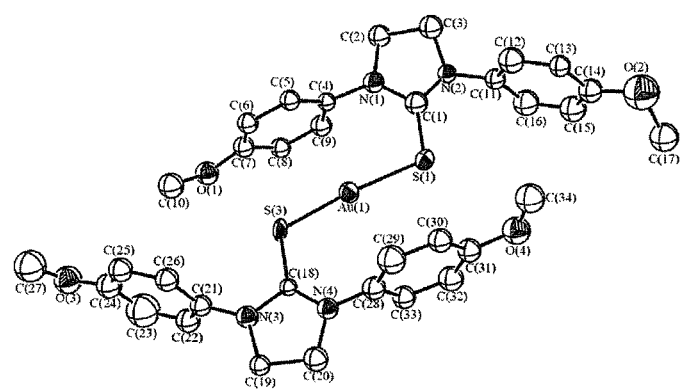
Fig. 3 ORTEP drawing of complex 1, [Au(TU)₂]Cl. Cl⁻ ion was omitted for clarity.

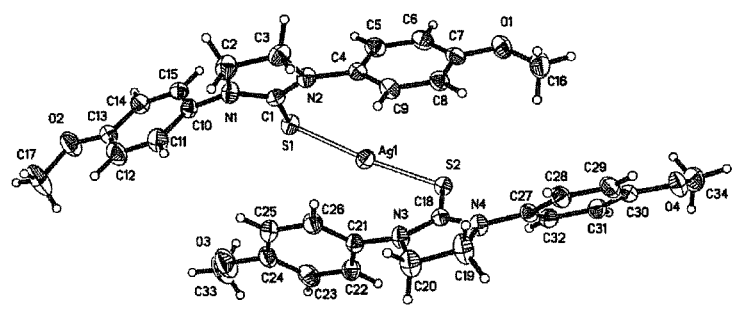
Fig. 4 ORTEP drawing of complex 2, [Ag(TU)₂]OTf. Triflate ion was omitted for clarity.

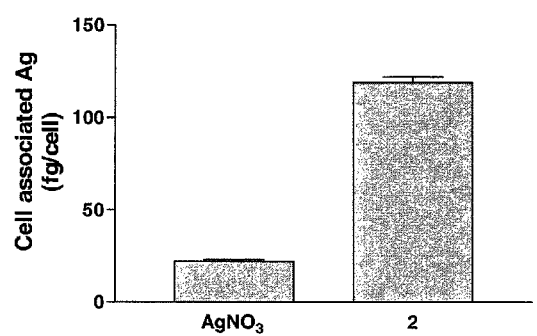
Fig. 5 Ag uptake of cells treated with complex 2 or AgNO$_3$

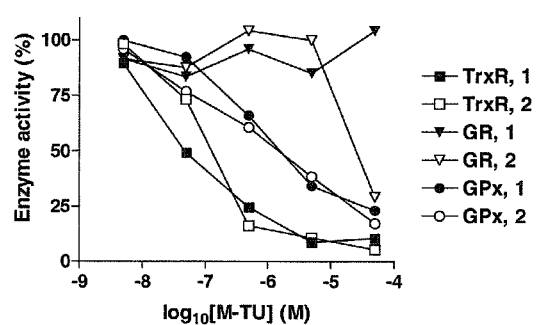
Fig. 6 Thioredoxin reductase (TrxR), glutathione reductase (GR) and glutathione peroxidase (GPx) activities of HeLa cells treated with complex 1 or 2 for 1 hour.

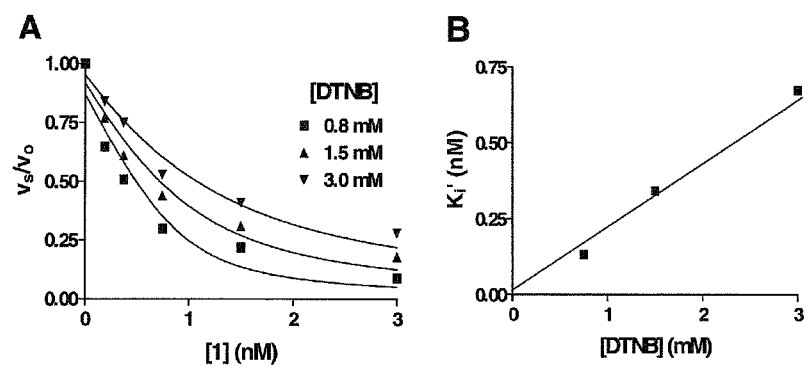
Fig. 7 Kinetic analysis of inhibition of TrxR preincubated with 1. A. Plot of relative steady state velocities against concentrations of 1. B. Plot of $K_i'$ against concentrations of DNTB substrate.

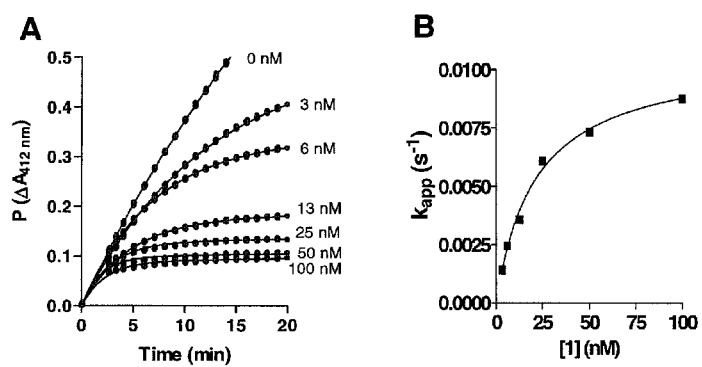
Fig. 8 Time dependence for the inhibition of TrxR by 1. A. Progress curve of rat TrxR in the absence or presence of 1. B. Plot of $k_{app}$ against concentrations of 1.

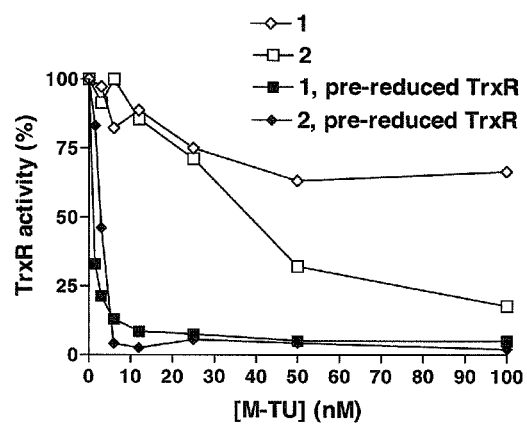
Fig. 9 Effects of pre-reduction of TrxR by NADPH on the enzyme inhibition by metal thiourea complexes.

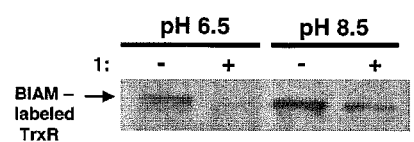
Fig. 10 Probing the free –SH and Se-H of TrxR treated with or without 1 by BIAM labelling

METAL COMPLEXES OF THIOUREA AND DERIVATIVES AS METAL DELIVERING ANTI-CANCER AND ANTI-INFLAMMATORY AGENTS

CROSS-REFERENCE TO RELATED APPLICATION

This application claims the benefit of U.S. Provisional Patent Application No. 61/328,829, filed on Apr. 28, 2010. The entire contents of the foregoing provisional application are incorporated herein by reference.

BACKGROUND OF THE INVENTION

Coinage metal (Au, Ag, Cu) ions exhibit distinct biological activities which could be harnessed to give effective therapeutic agents for anti-arithric, antimicrobial, and anti-cancer treatment.[1-6] The naked $M^{+0}$ ions, however, are unstable under physiological conditions and their instability such as that due to precipitation, aerobic oxidation and reduction can be circumvented by using appropriate auxiliary ligands. In literature, phosphine ligands are used to develop bioactive $d^{10}$ metals compounds though they are also cytotoxic.[7-9] Recent work has also witnessed new ligand systems such as N-heterocyclic carbenes.[10-13]

Thiourea ligands are well documented in coordination chemistry, and have recently been receiving an upsurge interest in the area of new metal catalysts. Nevertheless, biological studies on metal-thiourea complexes are sparse. This invention relates to coinage metal complexes of an N,N'-disubstituted cyclic thiourea which deliver significant cytotoxicties to cancer cells and in particular, gold(I) thiourea complex exhibits potent tight-binding inhibition of anticancer drug target thioredoxin reductase.

SUMMARY OF THE INVENTION

The invention provides a metal thiourea complex for treating cancer and inflammatory diseases, having the formula of Ia or Ib wherein $R_1$ can be H, alkyl, alkenyl, alkynl, aryl or heterocyclic groups; $R_2$ can be H, alkyl, alkenyl, alknyl or aryl groups; n=1 to 4; $X^-$ is a pharmaceutically acceptable anion (chloride, bromide, iodide, hexafluorophosphate, triflate) and M is a coinage metal (Au, Ag, or Cu).

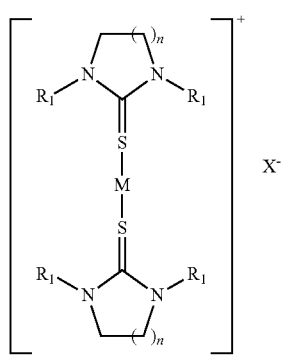

Ia

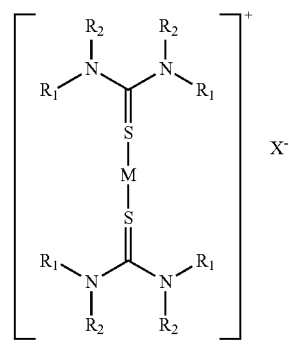

Ib

The invention further comprises a pharmaceutical composition comprising a compound as set forth above and a pharmaceutically acceptable vehicle, and can be used in a method to treat cancer or an inflammatory condition or disease.

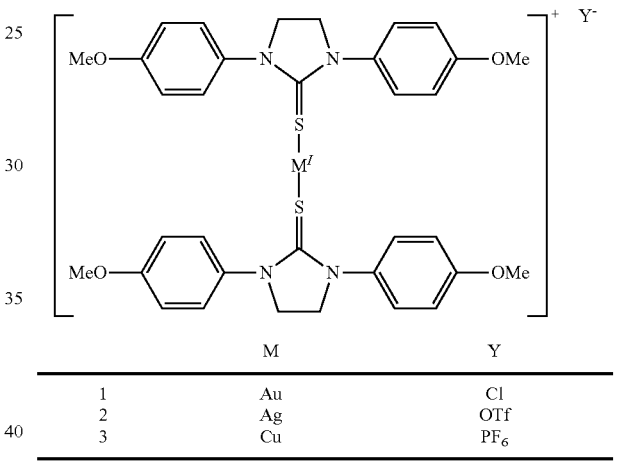

| | M | Y |
|---|---|---|
| 1 | Au | Cl |
| 2 | Ag | OTf |
| 3 | Cu | $PF_6$ |

The invention further provides a metal thiourea complex having the formula of IIa or IIb

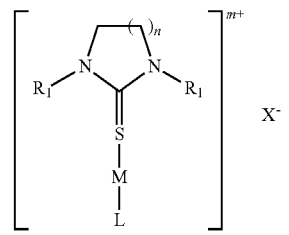

IIa

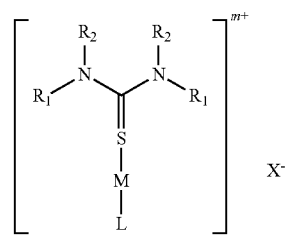

IIb wherein R$_1$ can be H, alkyl, alkenyl, alkynyl, aryl or heterocyclic groups;

R$_2$ can be H, alkyl, alkenyl, alkynl or aryl groups;

n=1 to 4;

X$^-$ is a pharmaceutically acceptable anion (chloride, bromide, iodide, hexafluorophosphate, triflate)

M is a coinage metal (Au, Ag, or Cu)

L can be halo, thiolate, thiourea, imine, amine, imidazole, phosphine, or carbene, m is the number of positive charge of the metal thiourea complex.

This compound composition can also be formed into a pharmaceutical composition using a pharmaceutically acceptable vehicle. The pharmaceutical composition may be used to treat cancer or an inflammatory condition or tissue by administering an amount of the composition effective to treat the inflammatory condition, disease, or cancer.

This invention further contemplates a method of treating cancer in a subject comprising administering to the subject an effective amount of the compounds of the invention.

The cancer may include breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, or acture lymphocytic leukemia comprising administering to the subject a therapeutically effective amount of one or more of the compounds of the invention, thereby treating the subject.

Embodiments of the present invention also provide compositions and methods for treating an inflammatory disorder with a therapeutically effective amount of one or more of the compounds of the present invention. The inflammatory disorder may occur in humans and comprise, for example, a form of arthritis, both adult and juvenile, psoriasis, inflammatory bowel disease atopic dermatitis, or bronchopulmonary dysplasia.

The invention further contemplates the use of prodrugs which are converted in vivo to the compounds of the invention (see, e.g., R. B. Silverman, 1992, "The Organic Chemistry of Drug Design and Drug Action", Academic Press, Chapter 8, the entire contents of which are hereby incorporated by reference). Such prodrugs can be used to alter the biodistribution (e.g., to allow compounds which would not typically enter a reactive site) or the pharmacokinetics of the compound.

The compounds described in the present invention are in racemic form or as individual enantiomers. The enantiomers can be separated using known techniques, such as those described, for example, in *Pure and Applied Chemistry* 69, 1469-1474, (1997) IUPAC.

"Solvent" as used herein is intended to include compounds such as, hexanes, benzene, toluene, diethyl ether, chloroform, methylene chloride, ethyl acetate, 1,4-dioxane, water, THF, acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene 1,1,2,2-tetrachloroethane, phenol, acetic acid, 1-butanol, 2-butanol, 2-butaone, diglyme, dimethylether, dioxane, petroleum ether, (NMP) N-methyl-2-pyrrolidinone, heptane, glycerin, HMPA (Hexamethylphosphorus triamide), MTBE (methyl t-butyl ether), nitromethane, pyrideine, 1-propanol, 2-propanol, and triethylamine.

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The instant compounds therefore may be in a salt form. As used herein, a "salt" is a salt of the instant compounds, which has been modified by making acid or base salts of the compounds. The salt may be pharmaceutically acceptable. Examples of pharmaceutically acceptable salts include, but are not limited to, mineral or organic acid salts of basic residues such as phenols. The salts can be made using an organic or inorganic acid. Such acid salts are chlorides, bromides, suflates, nitrates, phosphates, sulfonates, formats, tartrates, maleates, malates, citrates, benzoates, salicylates, ascorbates, and the like. Phenolate salts are the alkaline earth metal salts, sodium, potassium, or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, amleate, fumarate, succinate, tartrate, napthylate, mesylate, glucoheptonate, lactobionate, and laurylsuphonate salts and the like. For a description of possible salts, see, e.g., Berge et al., "Pharmaceutical Salts," *J. Phar. Sci.* 66:1-19 (1977).

As used herein, "therapeutically effective amount" means an amount sufficient to treat a subject afflicted with a disease or to alleviate a symptom or a complication associated with the disease. As used herein, "treating" means slowing, stopping or reversing the progression of a disease, particularly a form of cancer or inflammatory disease.

As used herein, "alkyl" is intended to include both branched and straight-chain saturated aliphatic hydrocarbon groups having 1-14 carbon atoms, preferably 1-10 carbon atoms, more preferably 1-6 carbon atoms, and most preferably 1-4 carbon atoms. For example, C$_1$-C$_{10}$, as in "C$_1$-C$_{10}$ alkyl" is defined to include groups having 1, 2, 3, 4, 5, 6, 7, 8, 9 or 10 carbons in a linear or branched arrangement. For example, "C$_1$-C$_{10}$ alkyl" specifically includes methyl, ethyl, n-propyl, i-propyl, n-butyl, t-butyl, i-butyl, pentyl, hexyl, heptyl, octyl, nonyl, decyl, and so on.

As used herein, the term "alkenyl" refers to a non-aromatic hydrocarbon radical, straight, branched or cyclic, containing from 2 to 10 carbon atoms, preferably 2 to 6 carbon atoms, and more preferably 2 to 4 carbon atoms, and at least one carbon to carbon double bond. Preferably one carbon to carbon double bond is present, and up to four non-aromatic carbon-carbon double bonds may be present. Thus, "C$_2$-C$_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, the term "alkynyl" refers to a hydrocarbon radical straight, branched or cyclic, containing from 2 to 10 carbon atoms, preferably 2 to 6 carbon atoms, and more preferably 2 to 4 carbon atoms, and at least one carbon to carbon triple bond. Up to three carbon-carbon triple bonds may be present. Thus, "C$_2$-C$_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

As used herein, "aryl" is intended to mean any stable monocyclic or bicyclic carbon ring of 4 to 14 atoms, preferably 4 to 10 atoms, more preferably 4 to 6 atoms, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

As used herein, the term "heterocycle" or "heterocyclyl" is intended to mean a 3- to 14-membered, preferably 3 to 10-membered, more preferably 3 to 6 nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein.

The above alkyl, alkenyl, alkynyl, cycloalkyl, aryl, heteroaryl and heterocyclyl substituents may be substituted or unsubstituted, unless specifically defined otherwise. The substituents may be selected from for example OH, oxo, halogen, $C_{1-6}$alkoxy, di($C_{1-6}$)alkylamino, or $C_{3-10}$heterocyclyl.

As appreciated by those of skill in the art, "halo" or "halogen" as used herein is intended to include chloro, fluoro, bromo and iodo.

As used herein, the term "pharmaceutically acceptable anion" is intended to include halide, for example, chloride, bromide, and iodide; phosphate, for example, hexafluorophosphate; and sulphate, for example, triflate.

As used herein, the term "coinage metal" is intended to include Au, Ag, and Cu, and so on.

The term "substituted" as used herein means that a given structure has a substituent which can be an alkyl, alkenyl, or aryl group as defined above. The term shall be deemed to include multiple degrees of substitution by a named substituent. Where multiple substituent moieties are disclosed or claimed, the substituted compound can be independently substituted by one or more of the disclosed or claimed substituent moieties, singly or plurally. By "independently substituted," it is meant that the (two or more) substituents can be the same or different.

As used herein, "administering" an agent may be performed using any of the various methods or delivery systems well know to those skilled in the art. The administering can be performed, for example, orally, parenterally, intraperitoneally, intravenously, intra-arterially, transdermally, sublingually, intramuscularly, rectally, transbuccally, intranasally, liposomally, via inhalation, vaginally, intraoccularly, via local delivery, subcutaneously, intra-adiposally, intra-articularly, intrathecally, into a cerebral ventricle, intraventicularly, intratumorally, into cerebral parenchyma or intraparenchchymally.

The following delivery systems, which employ a number of routinely used pharmaceutical carriers, maybe used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other celluslosic materials and starch), diluents (e.g., lactose and other sugars, starch, dicalcium phosphate and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcelluose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

BRIEF DESCRIPTION OF THE DRAWINGS

Further features and the advantages of the invention may be understood by reviewing the following detailed description of the preferred embodiments taken in connection with the attached drawings in which:

FIG. 1 is a schematic diagram of metal complexes of 1,3-bis(4-methoxyphenyl) imidazolidine-2-thione, $M(TU)_2Y$;

FIG. 2 is a synthetic route for the thiourea ligand;

FIG. 3 is an ORTEP drawing of complex 1, $[Au(TU)_2]Cl$, with the chloride ion (Cl⁻) omitted for clarity;

FIG. 4 is an ORTEL drawings of complex 2, $[Ag(TU)_2]$ OTf, with the triflate ion omitted for clarity;

FIG. 5 is a graph showing Ag uptake of cells treated with complex 2 or $AgNO_3$;

FIG. 6 is a graph showing thioredoxin reductase (TrxR), glutathione reductase (GR), and glutathione peroxidase (GPx) activities of HeLa cells treated with complex 1 or 2 for 1 hour;

FIG. 7 is a kinetic analysis of inhibition of TrxR preincubated with 1-A is a plot of relative steady state velocities against concentrations of 1; B is a plot of $K_i'$ against concentrations of DNTB substrate;

FIG. 8 is a plot of time dependence for the inhibition of TrxR by 1-A is a progress curve of rat TrxR in the absence or presence of 1; B is a pPlot of $k_{app}$ against concentrations of 1;

FIG. 9 is a plot of the effects of pre-reduction of TrxR by NADPH on the enzyme inhibition by metal thiourea complexes; and FIG. 10 is a photograph of a nitro-cellulose membrane in which BIAM labeled proteins were detected with horseradish peroxidase conjugated streptavidin and enhanced chemiluminescence detection.

DETAILED DESCRIPTION OF THE PREFERRED EMBODIMENTS

Herein described are the biological activities of a set of Au(I), Ag(I) and Cu(I) complexes supported by N,N'-disubstituted cyclic thiourea ligands, an example of which is 1,3-bis(4-methoxyphenyl)imidazolidine-2-thione (TU) (FIG. 1).

These are homoleptic complexes of general formula [M(TU)$_2$]Y, where M is Au(I), Ag(I) or Cu(I) ion. The molecular structures of [Au(TU)$_2$]Cl (1) and [Ag(TU)$_2$]OTf (2), have been established by X-ray crystallography [FIGS. 3 and 4; Table 1 and 2]. The M$^+$ ion in each case is coordinated by two thiourea ligands via the sulfur lone pair in a linear coordination geometry. The S-M-S bond angles (for 1, 175.1°; for 2, 172.7°) and M-S bond lengths (for 1, 2.236 Å; for 2, 2.407 Å) are similar to those found in the related Au(I) and Ag(I) complexes with other thiourea ligands (for 1, 2.278-2.406 Å; for 2, 166.7-180°, respectively).[14,15] There is no close intermolecular M...M distance found in 1 (>3.32 Å) and 2 (3.29 Å), suggesting that the intermolecular metal-metal interactions are weak.

All the metal thiourea complexes are stable in solid state in air, soluble as 10 mM solution in DMSO and maintain stability with negligible spectral change for a time period of 72 h. No precipitation occurred when these complexes were added up to 30 μM to serum supplemented cell culture medium.

The effect of metal thiourea complexes on the growth of a panel of cancer cell lines were investigated (Table 3). All the metal complexes exerted cytotoxicity at low micromolar concentrations, with half maximal inhibitory concentrations (IC$_{50}$) comparable to or lower than those of benchmark anticancer drug cisplatin. The IC$_{50}$ of metal-free thiourea ligand is more than 100 μM, suggesting that the biological activities of the metal complexes are largely metal mediated, and the lipophilic thiourea ligand serves as a nontoxic carrier of the metal ion to the cells. To test this notion, the activities of Ag(I) thiourea complex 2 and Ag$^+$ ions in the form of AgNO$_3$ solution were compared (FIG. 5). The Ag uptake of cells treated with 10 μM of 2 or 10 μM of AgNO$_3$ for 2 h were measured by ICP-MS. The data revealed that the Ag content in 2 treated HeLa cells was 5-fold higher than those treated with AgNO$_3$. Furthermore, the cytotoxic potency of 2 for HeLa cells is also nearly 5-fold higher than that of AgNO$_3$ (IC$_{50}$=32.1±1.2 μM).

The therapeutic potential of Au(I) has long attracted considerable interest. For example, Au(I)— thiolates (aurothiomalate) or phosphines (auranofin) are disease modifying anti-arthritic drugs, and have been recently studied for their anticancer properties.[16,17] We have examined the in vivo anti-cancer activities of 1 in mice inoculated with NCI-H460 non-small cell lung cancer cells (Table 4). Intraperitoneal injection of complex 1 at 100 mg/kg body weight for twice a week resulted in reduction in tumor size by (38%±11, n=5) compared to vehicle control after a 28-day treatment.

The exact molecular mechanism of action of Au(I) compounds has yet to be elucidated, but is generally related to facile ligand exchange with thiol groups, particularly those with low pK$_a$ values.[18,19] In this regard, the thioredoxin reductase (TrxR) is a compelling molecular target of Au(I).[20,21] The mammalian TrxR is a NADPH dependent selenocysteine-containing which plays a pivotal role in cancer progression and inflammatory diseases, and inhibitors of this enzyme are considered as promising therapeutic agents.[22,23] The effect of Au(I) thiourea complex 1 on cellular TrxR activity has been investigated. As shown in FIG. 6, an one-hour treatment of HeLa cancer cells with 1 resulted in an inhibition of the cellular TrxR activity with an IC$_{50}$ value of 50 nM. Another selenocysteine-containing thiol enzyme, glutathione peroxidase (GPx), was also inhibited by 1 albeit with at higher concentration (IC$_{50}$=1 μM). Glutathione reductase (GR) activity was not affected by 1. For comparison, Ag(I) thiourea complex 2 inhibited TrxR and GPx with IC$_{50}$ of 100 nM and 1 μM, respectively, which are almost of with similar potency to complex 1, and also significantly suppressed GR activities when added at 50 μM. All the enzyme activities were not affected by Cu(I) complex 3 or metal-free thiourea ligand added up to 100 μM. These data demonstrate that among the coinage M$^+$ ions, Au(I) preferentially targets the selenocysteine containing enzymes.

Our initial in vitro enzyme assays showed that half maximal inhibition of TrxR (1 nM) was obtained using approximately equal molar concentration of 1, suggestive of a tight-binding mode of inhibition. This was further studied by progress curve analysis (FIG. 8).[24,25] 1 was added in excess (3-100 nM) to a reaction mixture containing 0.2 mM NADPH, 1 nM TrxR and 3 mM disulfide substrate 5,5'-dithiobis(2-nitrobenzoic acid) (DTNB) in phosphate buffer (pH 7.4). The time course of change in the product concentrations at various concentrations of 1 are shown in FIG. 8A. The progress curves are non-linear, revealing two-phase equilibria typical of slow-onset tight-binding inhibition. This was analyzed using Eq. 1 (Example 6), where P is the product concentration, $v_i$ and $v_f$ are the initial and final steady-state velocities, respectively, and $k_{app}$ is the apparent first-order rate constant for establishment of the final steady-state inhibition. A plot of the $k_{app}$ against the inhibitor concentrations followed a hyperbolic function (FIG. 8B). This is indicative of a two-step, tight-binding inhibition mechanism:

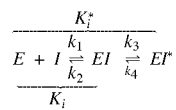

where EI is the initial collision complex, $k_3$ is the forward isomerization rate, and $k_4$ is the reverse isomerization rate. In this scheme, binding involves rapid formation of an initial collision complex (EI) that subsequently undergoes isomerization to the final slow dissociating enzyme-inhibitor complex (EI*). The $k_3$, $k_4$ and the dissociation constant of the initial collision complex EI (Ki') can be obtained by fitting the data to Eq. 2. Accordingly, $k_3$=0.011 s$^{-1}$, $k_4$=0.00014 s$^{-1}$ and K$_i$=1.39 nM. Thus, the tight binding inhibition is essentially irreversible, and in fact the enzyme activities could not be recovered after removal of the free inhibitors by ultrafiltration. The overall inhibitory constant K$_i$* was determined to be 18 pM using Eq. 3. These inhibitory constants are also reasonably close to the corresponding values determined from the steady state rate law established in condition when EI* was preformed, with K$_i$=0.67 nM and K$_i$*=36 pM (FIG. 7). 1 is thus among the most potent TrxR inhibitor reported.[20,23]

The reduced TrxR has free —SH (Cys496) and —SeH (Sec497) groups at the C-terminal active site, making it vulnerable to be attacked by Au(I). [20, 22, 23] These redox active sites can be probed by biotinylated iodoacetamide (BIAM), which alkylates the free —SH and —SeH groups; and the resulting adduct can be detected by western blot experiment using streptavidin-linked horseradish peroxidase (FIG. 10). [26, 27] It has been shown that these residues can be selectively alkylated by BIAM by adjusting the pH. At pH 8.5, both —SH and —SeH are alkylated. At pH 6.5, only the —SeH is alkylated owing to the low pKa value for selenocysteine, and thus a weaker streptavidin signal was obtained in which case. When NADPH reduced TrxR (0.1 μM) was preincubated with 1 (4 μM), the BIAM labeling at both pH 8.5 and pH 6.5 (buffered with 0.1 M Tris.HCl) was inhibited, suggesting that the selenocysteine or additionally the cysteine residues at the active site were involved in the enzyme inactivation. This is consistent with the observation that the NADPH reduced TrxR, which exposes the free —SH and —SeH groups, was much more efficiently inhibited by 1 than the oxidized TrxR having the —S—Se— group (FIG. 9). It is highly likely that the formation of the tight enzyme-inhibitor complex (EI*) involves covalent modification of the redox active selenocysteine and cysteine residue via the Au(I) complex. [28]

In summary, $d^{10}$ metal complexes supported by thiourea ligands represent a new paradigm in developing bioactive metal based complexes. In particular, we have demonstrated that the Au(I) thiourea complex confers specific tight binding inhibition of thioredoxin reductase with a potency among the lowest reported, [23] and exhibits effective suppression of cellular TrxR activity. By variation of thiourea ligand, the metal thiourea complexes have the prospect to be a new class of metal based drugs leads.

EXAMPLE 1

Synthesis of Metal Thiourea Complexes (FIG. 2)

Materials
Au(THT)Cl and [Cu(CH$_3$CN)$_4$]PF$_6$ were prepared according to literature procedures.[29, 30]

Thiourea ligand

Glyoxal-bis-(4-methoxyphenyl)imine[31]

To a solution of p-anisidine (12.3 g, 0.1 mol) in EtOH (50 mL) was added a mixture of 40% aqueous solution of glyoxal (7.3 g, 0.05 mol), EtOH (10 mL) and water (10 mL) at 25° C. The mixture was stirred overnight at 25° C. Upon addition of water (30 mL), a yellow solid precipitated which was collected by filtration and dried in vacuo. Yield: 5.5 g (82%). $^1$H NMR (400 MHz, CDCl$_3$): δ 8.42(s, 2H), 7.32(d, J=9.0, 4H), 6.96(d, J=9.0, 4H), 3.84 (s, 6H). $^{13}$C NMR (400 MHz, CDCl$_3$): δ 160.2, 158.0, 143.4, 123.4, 115.0, 55.9.

N,N'-Bis-(4-methoxyphenylamino)ethane[31]

A suspension of glyoxal-bis-(4-methoxyphenyl)imine (1.34 g, 5 mmol) in a mixture of THF (30 mL) and MeOH (5 mL) was treated at 0° C. with sodium borohydride (0.76 g, 20 mmol). The mixture was stirred overnight at 25° C. and subsequently heated for 2 h under reflux. Upon addition of ice-water (30 mL) and 3 M HCl (30 mL), a white solid precipitated which was collected by filtration and dried in vacuo. Yield: 1.2 g (88%). $^1$H NMR (400 MHz, CDCl$_3$): δ 6.79(d, J=8.92, 4H), 6.62(d, J=8.92, 4H), 3.75(s, 6H), 3.34 (s, 4H). $^{13}$C NMR (300 MHz, CDCl$_3$): δ 152.8, 142.7, 115.4, 114.9, 56.2, 44.9.

Thiourea
1,3-bis(4-methoxyphenyl)imidazolidine-2-thione (TU)[32]

To a solution of N,N'-Bis-(4-methoxyphenylamino)ethane (1.4 g, 5 mmol) in dry THF (40 mL) was added 1,1'-thiocarbonyl diimidazole (1.1 g, 6 mmol) at 25° C. The mixture was stirred overnight and subsequently heated for 2 h under reflux. After the addition of water and ethyl acetate, the organic layer was washed with dilute HCl and brine, dried and concentrated. The pure product was obtained through recrystallization from 95% EtOH. Yield: 1.1 g (70%). $^1$H NMR (400 MHz, CDCl$_3$): δ 7.42(d, J=8.96, 4H), 6.95(d, J=8.96, 4H), 4.10(s, 4H), 3.82 (s, 6H). $^{13}$C NMR (300 MHz, CDCl$_3$): δ 182.6, 158.6, 134.3, 127.6, 114.6, 55.9, 50.3. FAB-MS: 315 [M+H]$^+$.

Metal Complexes with Thiourea Ligand (1) [Au(TU)$_2$]Cl

To a CH$_2$Cl$_2$ (5 mL) solution of TU (0.31 g, 1 mmol) was added Au(THT)Cl (0.16 g, 0.5 mmol) in distilled MeOH (5 mL) under an argon atmosphere. The mixture was stirred at room temperature overnight and subsequently filtered. The filtrate was left standing overnight. Colorless crystals were collected and dried in vacuo. Yield: 76%. FAB-MS: m/z=826 [M]$^+$. $^1$H NMR (400 MHz, DMSO): δ 7.38(d, J=8.33, 4H), 7.42(d, J=8.35, 4H), 4.21(s, 4H), 3.77(s, 6H). IR (KBr, cm$^{-1}$): 2960(w), 2929(w), 2835(w), 1606(m), 1515(s), 1283(m), 1252(s), 1162(m), 1029(m), 836(s), 554(m). Anal. Calcd. for AuC$_{34}$H$_{36}$N$_4$O$_4$S$_2$Cl: C, 47.42; H, 4.21; N, 6.51. Found: C, 47.12; H, 4.00; N, 6.53.

(2) [Ag(TU)$_2$]OTf

Thiourea TU (0.31 g, 1 mmol) was dissolved in EtOH (10 mL) and silver triflate (0.13 g, 0.5 mmol) was added under an argon atmosphere. The mixture was stirred at room temperature for 3 h, and subsequently filtered to remove the unreacted AgOTf. The filtrate was left standing overnight. Colourless crystals were collected and dried in vacuo. Yield: 82%. FAB-MS: 736 [M]$^+$. $^1$H NMR (400 MHz, CDCl$_3$): δ 7.33(d, J=8.94, 4H), 6.93(d, J=8.91, 4H), 4.21(s, 4H), 3.71(s, 6H). IR (KBr, cm$^{-1}$): 2961(w), 2930(w), 2839(w), 1605(w), 1512(s), 1275(s), 1250(s), 1165(m), 1032(m), 831(s), 555(m). Anal. Calcd. for AgC$_{35}$H$_{36}$N$_4$O$_7$S$_3$F$_3$: C, 47.46; H, 4.10; N, 6.33. Found: C, 47.41; H, 4.15; N, 6.36.

(3) [Cu(TU)$_2$]PF$_6$

Thiourea TU (0.31 g, 1 mmol) was dissolved in CH$_2$Cl$_2$ (10 mL) and [Cu(CH$_3$CN)$_4$]PF$_6$ (0.19 g, 0.5 mmol) in distilled MeOH (10 mL) was added under an argon atmosphere. The mixture was stirred at room temperature for 2 h. The resulting white solid was filtered and washed with MeOH, Et$_2$O and dried in vacuo. Yield: 80%. FAB-MS: 692 [M]$^+$. $^1$H NMR (400 MHz, DMSO): δ 7.46(d, J=8.97, 4H), 6.96(d, J=8.90, 4H), 4.10(s, 4H), 3.76(s, 6H). IR (KBr, cm$^{-1}$): 2969(w), 2934(w), 2838(w), 1606(m), 1514(s), 1287(m), 1252(s), 1166(m), 1030(m), 838(s), 556(m). Anal. Calcd. for CuC$_{34}$H$_{36}$N$_4$O$_4$S$_2$PF$_6$: C, 48.77; H, 4.33; N, 6.69. Found: C, 48.12; H, 4.00; N, 6.32.

EXAMPLE 3

Cytotoxicity Assays (Table 3)

Cells were seeded in a 96-well flat-bottomed microplate at 20,000 cells/well in 150 μL of growth medium solution. The compounds were dissolved in dimethyl sulfoxide. Serial dilution of each complex was added to each well with final concentration of DMSO≤1%. The microplate was incubated at 37° C., 5% $CO_2$, 95% air in a humidified incubator for 72 h. After incubation, 10 μL MTT reagent (5 mg/mL) was added to each well. The microplate was re-incubated at 37° C. in 5% $CO_2$ for 4 h. Solubilization solution (10% SDS in 0.01 M HCl) (100 μL) was added to each well. The microplate was left in an incubator for 24 h. Absorbances at 550 nm were measured by a microplate reader. The $IC_{50}$ values (the concentration required to reduce the absorbance by 50% compared to the controls) were determined.

EXAMPLE 4

Metal Uptake by Cells (FIG. 5)

HeLa cells ($2 \times 10^5$ cells/well) were seeded in 12-well plate with culture medium (2 mL/well) and incubated at 37° C. in an atmosphere of 5% $CO_2$/95% air for 24 h. The culture medium was then removed and replaced with fresh medium containing 2 and $AgNO_3$ (10 μM). After exposure for 2 h, the medium was removed and the cell monolayer was washed three times with PBS. The cells were lysed with water and digested in 70% $HNO_3$ at 80° C. for 2 h. The digests were diluted with water to 10 mL for inductively coupled plasma mass spectrometry (ICP-MS) analysis.

EXAMPLE 5

Cellular Activities of Thiol-Dependent Redox Enzymes (FIG. 6)

Preparation of Cellular Extracts

Cells were seeded at $2 \times 10^5$/well in 6-well plates and incubated for 24 hours. The metal thiourea compounds ($10^{-9}$ to $10^{-4}$ M) were serially diluted and added to the cells (final DMSO concentrations≤1%). After an one-hour incubation, cells were washed thrice with phosphate buffered saline and 100 μL ice-cold lysis buffer (50 mM phosphate buffer, pH 7.4, 1 mM EDTA, 0.1% Triton-X 100) were added to the cell layer. Cell lysis was carried on ice for 5 minutes and the cell lysates were collected and stored at −80° C. or assayed immediately.

Thioredoxin Reductase (TrxR)

Cell lysates (10 μg proteins) were added to a mixture (100 μL) containing 100 mM phosphate, pH 7.4, 1 mM EDTA and 0.2 mM NADPH. Reaction was initiated by adding 5,5'-dithiobis(2-nitrobenzoic acid) (DTNB, 3 mM final) and the TrxR activities were determined as increases in $O.D._{412\,nM}$ in 10 min.

Glutathione Peroxidase (GPx)

Cell lysates (10 μg proteins) were added to a mixture containing 100 mM phosphate, pH 7.4, 2 mM GSH, 1 U glutathione reductase, and 0.2 mM NADPH. Reaction was initiated by adding tert-butyl hydroperoxide (300 μM) and the NADPH oxidation was measured as decreases in $O.D._{340\,nm}$ in 10 min. GPx activities ($\Delta O.D._{340\,nm}$/min) were determined by subtracting the spontaneous NADPH oxidation in the absence of tert-butyl hydroperoxide.

Glutathione Reductase (GR)

Cell lysates (10 μg proteins) were added to a mixture containing 100 mM phosphate, pH 7.4, 1 mM EDTA, 1 mM GSSG and 0.2 mM NADPH. Reaction was initiated by adding DTNB (3 mM final) and the increases in $O.D._{412\,nm}$ were measured for 10 min. GR activities were determined by subtracting the increases in $O.D._{412\,nm}$ in the absence of GSSG.

EXAMPLE 6

Kinetic Analysis of Tight-Binding Inhibition of Thioredoxin Reductase by Au-TU

Determination of Inhibitory Constant ($K_i$) Derived from Residual Activities of Preformed Enzyme-Inhibitor Complexes [33,34] (FIG. 7)

1 nM Recombinant rat TrxR1 (ICMO Corp, Sweden) was reduced with 0.2 mM NADPH and then incubated with 0.3-10 nM of 1 for 30 min in a buffer of 100 mM phosphate buffer, pH 7.4 and 1 mM EDTA. The residual activities were measured using 0.75, 1.5 or 3 mM DTNB (FIG. 7A). The data were fit into Eq. 1 using GraphPad Prism 3.0 software.

$$v_s/v_o=(E_t-K_i-I_t+((I_t+K_i'-E_t)^2+(4K_iE_t))^{1/2})/(2E_t) \quad (1)$$

Eq. 1 describes the rate law of tight-binding inhibition in which case the inhibitor concentration is substantially depleted owing to formation of enzyme-inhibitor complex. In this equation, $v_o$ is the observed velocity in the absence of inhibitor, $v_s$ is the steady-state velocity in the presence of inhibitor, $E_t$ is the total enzyme concentration, and I is the inhibitor concentration. The apparent inhibitory constant ($K_i$) so obtained was 0.67 nM. Average inhibitory constant ($K_i^*$) was calculated to be 36 pM using Eq. 2, (FIG. 7B) which takes into account of competitive inhibition of the enzyme with the substrate and a predetermined $K_m$ of 0.2 mM.

$$K_i=K_i^*(1+S/K_m) \quad (2)$$

Determination of $K_i$ by Progress Curve Analysis [35,36] (FIG. 8)

1 was added in excess (3-100 nM) to a reaction mixture containing 0.2 mM NADPH, 1 nM TrxR1, 3 mM disulfide substrate 5,5'-dithiobis(2-nitrobenzoic acid) (DTNB), 100 mM phosphate buffer, pH 7.4 and 1 mM EDTA. The time courses of change in the product concentration are shown in FIG. 8A. The progress curves are non-linear, showing two-phase equilibria typical of slow-onset tight-binding inhibition. The data was fit into Eq. 1 using GraphPad Prism 3.0 software, $$P=v_ft+((v_i-v_f/k_{app})(1-e^{-k_{app}t}) \quad (1)$$

where P is the product concentration, $v_i$ and $v_f$ are the initial and final steady-state velocities, respectively, and $k_{app}$ is the apparent first-order rate constant for establishment of the final steady-state inhibition. A plot of the $k_{app}$ against the inhibitor concentrations followed a hyperbolic function (FIG. 8B). This is indicative of a two-step, tight-binding inhibition mechanism:

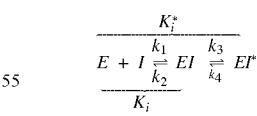

where EI is the initial collision complex, $k_3$ is the forward isomerization rate, and $k_4$ is the reverse isomerization rate. In this scheme, binding involves rapid formation of an initial collision complex (EI) that subsequently undergoes isomerization to the final slow dissociating enzyme-inhibitor complex (EI*). The $k_3$, $k_4$ and the dissociation constant of the initial collision complex EI ($K_i'$) can be obtained by fitting the data to Eq. 2.

$$k_{app}=k_4+k_3I_t(I_t+K_i'(1+S/K_m)) \quad (2)$$

where $I_t$ is the inhibitor concentration, S is the substrate (DTNB) concentration and $K_m$ is the Michaelis-Menten constant for reduction of DTNB by TrxR. Accordingly, $k_3$=0.011 $s^{-1}$, $k_4$=0.00014 $s^{-1}$ and $K_i'$=1.39 nM. The overall inhibitory constant $K_i^*$ was determined to be 18 pM using Eq. 3.

$$K_i^* = K_i'(k_4/(k_3+k_4)) \quad (3)$$

Effects of NADPH Reduction of TrxR1 Inhibition by Metal Thiourea Complexes (FIG. 9)

1 nM of TrxR1 was incubated with or without 0.2 mM NADPH in reaction buffer (100 mM phosphate, pH 7.4, 1 mM EDTA) for 5 min. metal thiourea complexes (1-100 nM) was added and allowed to incubate for 30 min. DTNB (3 mM) and NADPH (0.2 mM) was then added. The TrxR1 activities were determined as the increases in O.D.$_{412\,nm}$ over 10 min.

EXAMPLE 7

Probing the Cysteine and Selenocysteine Residues of TrxR1 [10-12] (FIG. 10)

NADPH-reduced TrxR1 (0.1 μM) and 1 (4 μM) were incubated in reaction buffer (100 mM phosphate buffer, pH 7.4, 1 mM EDTA) at room temperature for 1 h. 1 μL of the reaction mixture was taken out and added to new tubes containing 19 μL of 100 μM BIAM (buffered with 200 mM Tris-HCl at pH 6.5 and 8.5, respectively). The incubation was carried out at 37° C. for 30 min to alkylate the remaining free —SeH and —SH groups of the enzyme. 20 μL of the reaction mixtures were mixed with loading buffer and subjected to SDS-PAGE on a 7.5% gel. The separated proteins were transferred to nitrocellulose membrane and the BIAM labeled proteins were detected with horseradish peroxidase conjugated streptavidin and enhanced chemiluminescence detection.

EXAMPLE 8

Tumor Implantation in Nude Mice and In Vivo Drug Treatment (Table 4)

The in vivo experiment was conducted in Pearl Materia Medica Development (Shenzhen) Limited and performed with approval from the Committee on the Use of Live Animals for Teaching and Research. SPF grade four-week-old female BALB/c AnN-nu mice (nude mice, 16-18 g) were purchased. Tumor cells (5×10$^6$) resuspended in RPMI medium were implanted by subcutaneous injection on the right flank of the mice. When tumors were approximately 50 mm$^3$ in size, animals were randomly separated into 3 groups to receive treatment of twice-a-week intraperitoneal injection of 10% PET vehicle control (where 10% PET=6% polyethylene glycol 400, 3% ethanol, 1% Tween 80 and 90% PBS), complex 1 (100 mg/kg) or cyclophosphamide (30 mg/kg) for 8 times. After 28 days, the mice were sacrificed and the tumors were isolated and weighted.

REFERENCES

The following references are incorporated by reference herein:

1. M. Gielen and E. R. T. Tiekink, *Metallotherapeutic drugs and metal-based diagnostic agents: the use of metals in medicine*, J. Wiley, Chichester, England; Hoboken, N.J., 2005.
2. S. J. BernersPrice and P. J. Sadler, *Coordination Chemistry Reviews*, 1996, 151, 1-40.
3. C. X. Zhang and S. J. Lippard, *Current opinion in chemical biology*, 2003, 7, 481-489.
4. R. W. Sun, D. L. Ma, E. L. Wong and C. M. Che, *Dalton Trans*, 2007, 4884-4892.
5. C. F. Shaw, *Chemical Reviews*, 1999, 99, 2589-2600.
6. P. J. Barnard and S. J. Berners-Price, *Coordination Chemistry Reviews*, 2007, 251, 1889-1902.
7. S. J. Berners-Price, G. R. Girard, D. T. Hill, B. M. Sutton, P. S. Jarrett, L. F. Faucette, R. K. Johnson, C. K. Mirabelli and P. J. Sadler, *Journal of medicinal chemistry*, 1990, 33, 1386-1392.
8. M. J. McKeage, P. Papathanasiou, G. Salem, A. Sjaarda, G. F. Swiegers, P. Waring and S. B. Wild, *Met Based Drugs*, 1998, 5, 217-223.
9. E. R. Tiekink, *Bioinorg Chem Appl*, 2003, 53-67.
10. P. J. Barnard, M. V. Baker, S. J. Berners-Price and D. A. Day, *J Inorg Biochem*, 2004, 98, 1642-1647.
11. K. M. Hindi, T. J. Siciliano, S. Durmus, M. J. Panzner, D. A. Medvetz, D. V. Reddy, L. A. Hogue, C. E. Hovis, J. K. Hilliard, R. J. Mallet, C. A. Tessier, C. L. Cannon and W. J. Youngs, *Journal of medicinal chemistry*, 2008, 51, 1577-1583.
12. M. L. Teyssot, A. S. Jarrousse, A. Chevry, A. De Haze, C. Beaudoin, M. Manin, S. P. Nolan, S. Diez-Gonzalez, L. Morel and A. Gautier, *Chemistry-a European Journal*, 2009, 15, 314-318.
13. S. Ray, R. Mohan, J. K. Singh, M. K. Samantaray, M. M. Shaikh, D. Panda and P. Ghosh, *Journal of the American Chemical Society*, 2007, 129, 15042-15053.
14. L. C. Porter, J. P. Fackler, J. Costamagna and R. Schmidt, *Acta Crystallographica Section C-Crystal Structure Communications*, 1992, 48, 1751-1754.
15. O. E. Piro, E. E. Castellano, R. C. V. Piatti, A. E. Bolzan and A. J. Arvia, *Acta Crystallographica Section C-Crystal Structure Communications*, 2002, 58, M252-M255.
16. R. M. Snyder, C. K. Mirabelli and S. T. Crooke, *Seminars in arthritis and rheumatism*, 1987, 17, 71-80.
17. E. R. Tiekink, *Inflammopharmacology*, 2008, 16, 138-142.
18. S. S. Gunatilleke and A. M. Barrios, *Journal of medicinal chemistry*, 2006, 49, 3933-3937.
19. D. Krishnamurthy, M. R. Karver, E. Fiorillo, V. Orru, S. M. Stanford, N. Bottini and A. M. Barrios, *Journal of medicinal chemistry*, 2008, 51, 4790-4795.
20. S. Gromer, L. D. Arscott, C. H. Williams, Jr., R. H. Schirmer and K. Becker, *The Journal of biological chemistry*, 1998, 273, 20096-20101.
21. M. P. Rigobello, G. Scutari, A. Folda and A. Bindoli, *Biochemical pharmacology*, 2004, 67, 689-696.
22. E. S. Arner and A. Holmgren, *Seminars in cancer biology*, 2006, 16, 420-426.
23. S. Urig and K. Becker, *Seminars in cancer biology*, 2006, 16, 452-465.
24. J. F. Morrison and C. T. Walsh, *Advances in enzymology and related areas of molecular biology*, 1988, 61, 201-301.
25. M. J. Sculley, J. F. Morrison and W. W. Cleland, *Biochimica et biophysica acta*, 1996, 1298, 78-86.
26. J. R. Kim, H. W. Yoon, K. S. Kwon, S. R. Lee and S. G. Rhee, *Anal Biochem*, 2000, 283, 214-221.
27. J. Fang and A. Holmgren, *Journal of the American Chemical Society*, 2006, 128, 1879-1885.
28. J. L. Hickey, R. A. Ruhayel, P. J. Barnard, M. V. Baker, S. J. Berners-Price and A. Filipovska, *Journal of the American Chemical Society*, 2008.
29. R. Uson, A. Laguna, M. Laguna *Inorg. Syn.* 1989, 26, 85-91.
30. G. J. Kubas *Inorg. Syn.* 1990, 28, 68-70.

31. A. J. Arduengo, R. Krafczyk, R. Schmutzler, H. A. Craig, J. R. Goerlich, W. J. Marshall, M. Unverzagt *Tetrahedron* 1999, 55, 14523-14534.
32. D. Yang, Y. C. Chen, N.Y. Zhu *Organ. Lett.* 2004, 6, 1577-1580.
33. Chang, C. F.; Ho, C. W.; Wu, C. Y.; Chao, T. A.; Wong, C. H.; Lin, C. H. *Chem Biol* 2004, 11, 1301-6.
34. Vathipadiekal, V.; Rao, M. *J Biol Chem* 2004, 279, 47024-33.
35. Xu, C.; Hall, R.; Cummings, J.; Raushel, F. M. *J Am Chem Soc* 2006, 128, 4244-5.
36. Koh, C. Y.; Kazimirova, M.; Trimnell, A.; Takac, P.; Labuda, M.; Nuttall, P. A.; Kini, R. M. *J Biol Chem* 2007, 282, 29101-13.

TABLE 1

| Selected bond length (Å) and bond angles (°) of 1 | | | |
|---|---|---|---|
| Au(1)—S(1) | 2.356(8) | S(1)—Au(1)—S(3) | 175.1(3) |
| Au(1)—S(3) | 2.236(7) | C(1)—S(1)—Au(1) | 108.8(8) |
|  |  | C(18)—S(3)—Au(1) | 113.0(6) |

Symmetry transformations used to generate equivalent atoms: #1 −x + 1, −y, −z + 1.

TABLE 2

| Selected bond length (Å) and bond angles (°) of 2. | | | |
|---|---|---|---|
| Ag(1)—S(1) | 2.4067(11) | S(1)—Ag(1)—S(2) | 172.77(4) |
| Ag(1)—S(2) | 2.4075(10) | C(1)—S(1)—Ag(1) | 104.11(12) |
| Ag(1)—Ag(1)#1 | 3.2894(7) | C(18)—S(2)—Ag(1) | 104.88(12) |

Symmetry transformations used to generate equivalent atoms: #1 −x + 1, −y, −z + 1.

TABLE 3

| Cytotoxicities (IC$_{50}$) of metal thiourea complexes toward selected human cancer cell lines | | | | |
|---|---|---|---|---|
|  | HeLa | HepG2 | SUNE1 | NCI-H460 |
| 1 | 14.6 ± 0.7 | 17.4 ± 1.0 | 10.8 ± 0.2 | 3.72 ± 0.3 |
| 2 | 7.2 ± 0.7 | 4.0 ± 0.4 | 8.8 ± 1.0 | 8.86 ± 1.0 |
| 3 | 12.7 ± 0.9 | 13.0 ± 0.9 | 8.5 ± 1.0 | 11.15 ± 0.9 |
| TU | >100 | >100 | >100 | >100 |
| cisplatin | 4.7 ± 0.3 | 14.2 ± 1.0 | 35.2 ± 0.3 | 38.57 ± 0.4 |

HeLa, human cervical epithelioid carcinoma; HepG2, human hepatocellular carcinoma; SUNE1, human nasopharyngeal carcinoma; NCI-H460 = human lung carcinoma

TABLE 4

| Tumour implantation in nude mice and in vivo drug treatment (no. of mice: 5) | | | |
|---|---|---|---|
| | Tumor volume/mm$^3$ | | |
| | Vehicle control | Positive control (cyclophosphamide) (Dose: 30 mg · kg$^{-1}$) | [Au$^I$(TU)$_2$]Cl (1) (Dose: 100 mg · kg$^{-1}$) |
| Day 9 | 317.802 ± 308.863 | — | 209.026 ± 94.749 |
| Day 13 | 1420.931 ± 625.165 | 325.041 ± 170.053 | 624.380 ± 233.051 |
| Day 17 | 2336.166 ± 787.199 | 639.465 ± 422.362 | 1232.177 ± 229.411 |
| Day 21 | 2801.906 ± 1304.491 | 1032.258 ± 594.026 | 1834.856 ± 215.456 |
| Day 25 | 3650.140 ± 1721.593 | 1474.100 ± 900.357 | 2389.133 ± 594.756 |
| Day 29 | 4437.245 ± 222.022 | 1438.735 ± 845.815 | 2741.851 ± 805.220 |

What is claimed is:

1. A metal thiourea complex having the formula of Ia or Ib:

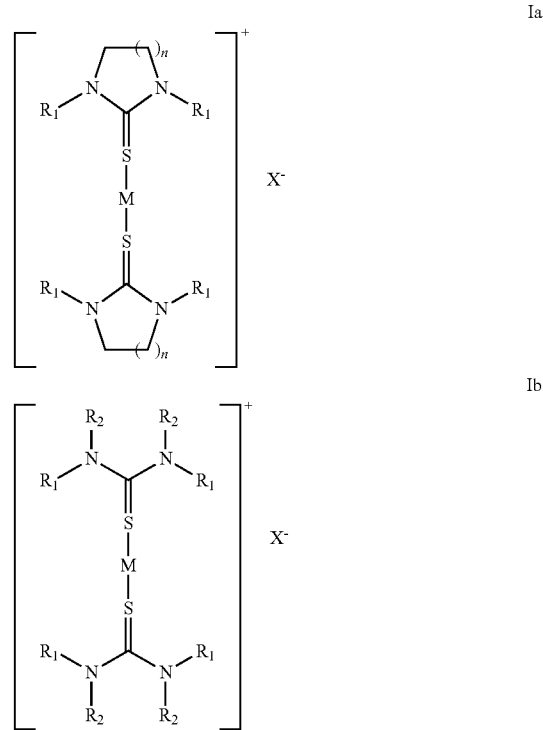

wherein $R_1$ is a methoxy substituted phenyl group;
 $R_2$ is a substituted or unsubstituted $C_{1-6}$alkyl, $C_{2-6}$alkenyl, $C_{2-6}$alkynl, or $C_{4-10}$aryl;
 n=1 to 4;
 $X^-$ is chloride, bromide, iodide, hexafluorophosphate, or triflate; and
 M is a Au, A or Cu for formula Ia and M is Au or Cu for formula Ib.

2. A pharmaceutical composition comprising the complex of claim 1 and a pharmaceutically acceptable vehicle.

3. A metal thiourea complex which is:
 [Au(TU)$_2$]Cl, Di(1,3-bis(4-methoxyphenyl)imidazolidine-2-thione)gold(I) chloride;
 [Ag(TU)$_2$]OTf, Di(1,3-bis(4-methoxyphenyl)imidazolidine-2-thione)silver(I) trifluoromethanesulfonate; or
 [Cu(TU)$_2$]PF$_5$, Di(1,3-bis(4-methoxyphenyl)imidazolidine-2-thione)copper(I) hexafluorophosphate.

4. A pharmaceutical composition comprising the metal thiourea complex of claim 3 and a pharmaceutically acceptable vehicle.

* * * * *